United States Patent
Butley et al.

(10) Patent No.: US 9,644,155 B2
(45) Date of Patent: May 9, 2017

(54) INTEGRATED PROCESS FOR PRODUCTION OF HIGH OCTANE GASOLINE, HIGH AROMATIC NAPHTHA AND HIGH CETANE DIESEL FROM HIGH AROMATIC MIDDLE DISTILLATE RANGE STREAMS

(71) Applicant: INDIAN OIL CORPORATION LTD., Mumbai, Maharashtra (IN)

(72) Inventors: Ganesh Vitthalrao Butley, Faridabad (IN); Mainak Sarkar, Faridabad (IN); Yamini Gupta, Faridabad (IN); Arangarasu Arun, Faridabad (IN); Madhusudan Sau, Faridabad (IN); Vatsala Sugumaran, Faridabad (IN); Vivekanand Kagdiyal, Faridabad (IN); Paramasivam Sakthivel, Faridabad (IN); Brijesh Kumar, Faridabad (IN); Biswapriya Das, Faridabad (IN)

(73) Assignee: INDIAN OIL CORPORATION LTD., Mumbai (IN)

( * ) Notice: Subject to any disclaimer, the term of this patent is extended or adjusted under 35 U.S.C. 154(b) by 0 days.

(21) Appl. No.: 14/658,036

(22) Filed: Mar. 13, 2015

(65) Prior Publication Data
US 2015/0267130 A1 Sep. 24, 2015

(30) Foreign Application Priority Data
Mar. 24, 2014 (IN) .......................... 985/MUM/2014

(51) Int. Cl.
| | |
|---|---|
| *C10G 65/12* | (2006.01) |
| *C10G 65/08* | (2006.01) |
| *C10L 1/02* | (2006.01) |
| *C10L 1/06* | (2006.01) |

(52) U.S. Cl.
CPC ............. *C10G 65/12* (2013.01); *C10G 65/08* (2013.01); *C10L 1/026* (2013.01); *C10L 1/06* (2013.01); *C07C 2102/10* (2013.01); *C10G 2300/305* (2013.01); *C10G 2300/307* (2013.01); *C10G 2400/02* (2013.01); *C10G 2400/04* (2013.01); *C10L 2270/023* (2013.01); *C10L 2270/026* (2013.01)

(58) Field of Classification Search
None
See application file for complete search history.

(56) References Cited

U.S. PATENT DOCUMENTS

| | | | |
|---|---|---|---|
| 4,723,963 A | 2/1988 | Taylor | |
| 4,828,676 A | 5/1989 | Sawyer et al. | |
| 4,985,134 A | 1/1991 | Derr, Jr. et al. | |
| 4,990,239 A | 2/1991 | Derr, Jr. et al. | |
| 7,265,252 B1 | 9/2007 | Frey et al. | |
| 7,271,303 B1 | 9/2007 | Sechrist et al. | |
| 7,368,619 B1 | 5/2008 | Frey et al. | |
| 7,384,542 B1 | 6/2008 | Thakkar et al. | |
| 7,501,054 B2 | 3/2009 | Galiasso | |
| 7,501,374 B2 | 3/2009 | Galiasso | |
| 7,622,034 B1 * | 11/2009 | Thakkar ................. | C10G 45/02 208/106 |
| 7,837,860 B1 | 11/2010 | Hoehn et al. | |
| 8,066,867 B2 | 11/2011 | Dziabala et al. | |
| 8,404,103 B2 | 3/2013 | Dziabala et al. | |
| 2012/0043257 A1* | 2/2012 | Dziabala ................. | C10G 65/12 208/57 |
| 2012/0205285 A1* | 8/2012 | Dindi ..................... | C10G 45/08 208/49 |

* cited by examiner

*Primary Examiner* — Brian J Davis
(74) *Attorney, Agent, or Firm* — Maschoff Brennan (57) ABSTRACT

An integrated process for production of ultra low sulfur products of high octane gasoline, high aromatic naphtha and high Cetane Diesel from high aromatic middle distillate range streams from any cracker units such as Light Cycle Oil (LCO) stream of Fluid catalytic cracking (FCC) units and subjected to hydrotreating for removal of heteroatoms like sulfur and nitrogen. The effluent from hydrotreating is subjected to hydrocracking at same pressure of hydrotreating step above for selective opening of saturated ring of multi-ring aromatics. The effluent from hydrocracking is separated in CUT-1, CUT 2 in which the monoaromatics and alkylated monoaromatics are concentrated and CUT-3 in which concentration of saturates significantly increased. The CUT-3 is selectively oxidized in selective oxidation step in presence of catalyst, an oxidizing agent and operating conditions such that it results in diesel product with more enhanced Cetane.

12 Claims, 2 Drawing Sheets

INTEGRATED PROCESS FOR PRODUCTION OF HIGH OCTANE GASOLINE, HIGH AROMATIC NAPHTHA AND HIGH CETANE DIESEL FROM HIGH AROMATIC MIDDLE DISTILLATE RANGE STREAMS

FIELD OF THE INVENTION

The present invention relates to an integrated process for upgradation of low value high aromatic feed stocks to high value products of High Octane Gasoline having octane value of at least 84, High Aromatic Naphtha having value of at least 90 and High Cetane Diesel having cetane number of at least 42 by integrating hydrotreating, hydrocracking processes with selective oxidation of diesel cut obtained from hydrocracking for further enhancement of cetane. More particularly the cetane number is enhanced by another 2 to 15 units.

BACKGROUND OF THE INVENTION

Low value high aromatic middle distillate range streams from any cracker units such as Light Cycle Oil (LCO) stream of Fluid catalytic cracking (FCC) units, because of high Sulphur, Nitrogen and Aromatic content; are very low value streams. Historically, these streams were being used as blend stocks in middle distillate and as cutter stock in fuel oil. Because of growing environmental consciousness the emission norms are getting stringent and at the same time the demand for high quality ultra low sulphur diesel (ULSD) is increasing rapidly. Therefore, these streams can no longer be used directly as diesel pool blending stocks. Further, the worldwide demand of Fuel oil is also declining sharply hence another conventional usage of these types of low value high aromatic streams as cutter stock has also become significantly low. Presently, in most of the refineries, these streams are being blended and hydrotreated along with diesel hydrotreater (DHDT) feed. In some refineries, these are also hydrocracked along with Vacuum Gas Oil (VGO) in a high pressure hydrocracker. But hydrotreating these streams for Diesel pool blending stock is inefficient means of utilizing costly hydrogen since hydrotreating only removes sulphur but cetane number remains much below the limit of Euro-III/IV/V diesel pool Cetane specification. Hydrocracking these streams along with VGO in conventional high pressure hydrocrackers improve diesel yield, but at the same time also increases naphtha generation substantially. Moreover, processing these streams in VGO hydrocracker also reduce throughput of VGO. Consequently, with both these options actual potential of high aromatics middle distillate range streams remains underutilized.

The middle distillate range streams of cracker units such as LCO stream of FCC units are rich in aromatic compounds. Depending upon the severity of the operating conditions the total aromatics in these types of streams vary from 50 to 90 wt %, in which mono-aromatic compounds are only 20-30 wt %, whereas di-aromatics are 50-70 wt % and the rest 5-10 wt % are polycyclic aromatic type of compounds. However, the poly-aromatic types of compounds present in these types of streams rarely have more than 3 rings.

The middle distillate range streams boiling between 150 and 400° C. are often considered as low value streams owing to their high aromaticity and high sulfur and nitrogen levels, since these streams are difficult to accommodate in diesel pool. Examples of such streams are light cycle oil (LCO) from FCC and Coker Gas Oil from Delayed Coker units. These low value streams in refineries have very low cetane values, thus accommodating them in diesel pool requires higher consumptions of costly hydrogen. Merely hydrotreating them to improve their qualities is very inefficient means of utilizing hydrogen. The judicious use of hydrotreating, hydrocracking with ring opening functionality in staged manner is required. For example, only hydrotreating these streams may result in diesel range product with poor cetane and hydrotreating with conventional hydrocracking in existing hydrocrackers may result in high yield losses in terms of lighter products of light naphtha and heavy naphtha of inferior quality with medium quality diesel range product. Further, these streams constitute high levels of aromatics which are valuable in some fields of art. If they are converted to utilizable compounds, they can be very good feed stock for petrochemical products. Therefore, it is preferable to convert these aromatics in more valuable and usable compounds and use rest of the portion rich in naphthenes and paraffins as diesel can be a viable and economical option for refiners.

Different techniques of conversion of highly aromatic, low value middle distillate streams of cracker units into high value, high octane motor gasoline, and USLD have been described in many patents, such as U.S. Pat. No. 8,404,103 described the technique of conversion of highly aromatic feeds such as LCO into low sulphur diesel and high octane naphtha using mild hydrotreating and hydrocracking reactions. In this patent it has been claimed that the octane quality of the gasoline or naphtha fraction can be improved by allowing slippage of organic nitrogen to hydrocracker reactor by optimizing the operating condition of the hydrotreater. The patent also claims to obtain naphtha having at least 50 wt % mono aromatics concentration with RON value at least 85 and diesel with sulphur concentration less than 10 ppmw.

The U.S. Pat. No. 8,066,867 claims to develop process for converting LCO into low sulphur diesel and high octane naphtha using mild hydrotreating and hydrocracking reaction. The patent also claims to produce naphtha with RON value at least 85 units and diesel with sulphur content less than 10 wt-ppm.

The U.S. Pat. No. 7,837,860 describes an integrated process for hydrodesulfurization of middle distillate streams and hydrocracking of highly aromatic hydrocarbon streams such as LCO for production of low sulphur diesel and high octane naphtha.

The U.S. Pat. No. 7,384,542 describes about the invention of process for production of low sulphur diesel and high octane naphtha form highly aromatic and substantially dealkylated streams like LCO. The process claims to produce mono-cyclic aromatic compounds having boiling points in the range of naphtha.

The U.S. Pat. No. 4,990,239 of Mobil Oil Corporation describes their invention for production of Gasoline and distillate fuels from Light Cycle Oil. The patent claims to produce Gasoline with RON value at least 87 units and low sulphur diesel with cetane value at least 30. Another patent, U.S. Pat. No. 4,985,134 from the same assignee claims to produce gasoline and diesel fuel of cetane number at least 35 from LCO.

U.S. Pat. No. 4,828,676 discloses a process for production of ultra high octane gasoline from Aromatic distillates using hydrocracking reaction. In their process, they have disclosed to use iron as one of the components in the catalyst for ring opening purpose.

Some patents are also available where highly aromatics and dealkylated streams like LCO has been converted into Petrochemical feed stocks and xylenes. The U.S. Pat. No. 7,368,619 discussed about the process where diesel and aromatic compounds including xylene have been produced from LCO. The U.S. Pat. No. 7,271,303 claims to develop a process for producing diesel and aromatic compounds integrating hydrocracking and catalytic reforming. Another patent U.S. Pat. No. 7,265,252 discloses production of Xylene from LCO by selective hydrocracking reaction.

The common shortcoming in all of the above discussed inventions is the property of ULSD which is produced as one of the streams during the process. Although diesel produced in the process is low in sulphur but the other properties such as Cetane Number remains much lower than that required for EURO-III/IV/V diesel pool. Therefore, for complete upgradation of these types of high aromatic middle distillate range cracker streams, the cetane of the ULSD produced during the process also needs to be improved.

The U.S. Pat. No. 4,723,963 of Exxon Research and Engineering Company discussed about invention on selective oxidation of aromatic compounds for improve of cetane rating of middle distillate. The patent claims that oxidation of aromatics particularly alkylaromatics and hydroaromatics at benzylic position improves the cetane rating of the fuel. The patent has also disclosed the cetane rating of different aromatic compounds normally present in middle distillate range fuels and their corresponding oxidized compounds.

U.S. Pat. No. 7,501,054 and U.S. Pat. No. 7,501,374 discuss about the invention of process and catalyst for upgrading diesel fuel by introducing oxygen. The patent also discloses a process to convert alkyl-naphthene-aromatics compound to alkyl ketones.

It is therefore, important to develop an integrated process of interest that can upgrade these types of high aromatic content middle distillate range streams of cracker units into value added products keeping view that all potential are utilized to their limits.

SUMMARY OF THE INVENTION

Accordingly, the present invention provides an integrated process for production of High Octane Gasoline, High Aromatic Naphtha and High Cetane Diesel, the process comprising:
a. subjecting a feed to hydrotreating step at a predetermined pressure to obtain a first effluent having a substantially reduced quantity of hetero-atoms compared to the feed, the feed comprising at least 30 wt % multi-ring aromatics and having boiling point between 200 to 400° C., wherein the predetermined pressure is capable to saturate one or more rings of multi-ring aromatics and to remains unsaturated one or more rings of the multi-ring aromatics;
b. subjecting the first effluent to a hydrocracking step at the predetermined pressure to obtain a second effluent, the hydrocracking step resulting in selective opening of at least one saturated ring of the multi-ring aromatics;
c. separating the second effluent into a CUT-1, a CUT-2 and a CUT-3, with the CUT-1 having a boiling point between 35 to 70° C., the CUT-2 having boiling point between 70 to 200° C. and comprising an enhanced concentration of mono aromatics and alkylated mono aromatics and the CUT-3 having boiling point above 200° C. and comprising an enhanced concentration of saturates; and
d. subjecting at least a part of the CUT-3 to a selective oxidation step to in presence of catalyst, an oxidizing agent to obtain diesel range product with enhanced cetane number.

In one of the embodiment, the present invention provides an integrated process for production of High Octane Gasoline, High Aromatic Naphtha and High Cetane Diesel, the process comprising:
a. subjecting a feed to hydrotreating step at a predetermined pressure to obtain a first effluent having a substantially reduced quantity of hetero-atoms compared to the feed, the feed comprising at least 30 wt % multi-ring aromatics and having boiling point between 200 to 400° C., wherein the predetermined pressure is capable to saturate one or more rings of multi-ring aromatics and to remains unsaturated one or more rings of the multi-ring aromatics;
b. separating the first effluent into a first part and a second part;
c. subjecting the first part of the first effluent to a hydrocracking step at the predetermined pressure to obtain a second effluent, the hydrocracking step resulting in selective opening a saturated ring of the multi-ring aromatics;
d. combining the second part of the first effluent with the second effluent to obtain a third effluent;
e. separating the third effluent into a CUT-1, a CUT-2 and a CUT-3, with the CUT-1 having a boiling point between 35 to 70° C., the CUT-2 having boiling point between 70 to 200° C. and comprising an enhanced concentration of mono aromatics and alkylated mono aromatics and the CUT-3 having boiling point above 200° C. and comprising an enhanced concentration of saturates; and
f. subjecting at least a part of the CUT-3 to a selective oxidation step to in presence of catalyst, an oxidizing agent to obtain diesel range product with enhanced cetane number.

According to the present invention, wherein a remaining part of the CUT-3 is mixed with the first part of the first effluent and subjected to the hydrocracking step at the predetermined pressure to obtain the second effluent.

In one of the embodiment, the present invention provides an integrated process for production of ultra low sulfur products of high octane Gasoline, high aromatic Naphtha and high Cetane Diesel and the process comprising:
a. a feed comprising at least 30 wt % multi-ring aromatics and having boiling point between 200 to 400° C.;
b. the feed is subjected to hydrotreating step for removal of heteroatoms and at a pressure sufficient only for saturation of one ring of multi-ring aromatics to obtain a first effluent;
c. the effluent from hydrotreating step along with effluent from hydrocracking step below (d) is separated in CUT-1 boiling between 35 to 70° C., CUT-2 boiling between 70 to 200° C. in which the monoaromatics and alkylated monoaromatics are concentrated and CUT-3 boiling above 200° C. in which concentration of saturates is significantly increased;
d. part of the CUT-3 from above (c) is subjected to hydrocracking at same pressure of hydrotreating step above for selective opening of saturated ring of multi-ring aromatics; and
e. the CUT-3 from above (c) is selectively oxidized in selective oxidation step in presence of catalyst system, an oxidizing agent and operating conditions in order to obtain diesel product with more enhanced cetane.

According to one embodiment of the present invention, the part of the CUT-3 is sent as feed to hydrocracking step and remaining part is recovered and sent to selective oxidation step.

According to another embodiment of the present invention, the part of the CUT-3 which is sent to the hydrocracking step is in the range of 30 to 70 wt % of totally CUT-3.

In one of the embodiment, the present invention provides an integrated process for production of ultra low sulfur products of high octane Gasoline, high aromatic Naphtha and high Cetane Diesel and the process comprising:
  a. a feed comprising at least 30 wt % multi-ring aromatics and having boiling point between 200 to 400° C.;
  b. the feed is subjected to hydrotreating for removal of heteroatoms and at a pressure sufficient only for saturation of one ring of multi-ring aromatics to obtain a first effluent;
  c. the first effluent from hydrotreating is subjected to hydrocracking at same pressure of hydrotreating step above for selective opening of saturated ring of multi-ring aromatics to obtain a second effluent;
  d. the second effluent from hydrocracking is separated in CUT-1 boiling between 35 to 70° C., CUT-2 boiling between 70 to 200° C. in which the monoaromatics and alkylated monoaromatics are concentrated and CUT-3 boiling above 200° C. in which concentration of saturates significantly increased;
  e. the CUT-3 from above (d) is further subjected to hydrotreating for producing product of sulfur content of below 10 ppm;
  f. the CUT-3 from above (e) after hydrotreating is selectively oxidized in selective oxidation step to in presence of catalyst, an oxidizing agent and operating conditions in order to obtain diesel product with more enhanced cetane.

In yet another embodiment of the present invention, the CUT-3 after selective oxidation Step (f) is having cetane number of at least 42.

In yet another embodiment of the present invention, the CUT-1 corresponds to ultra-low sulfur products of high octane Gasoline and octane number of the CUT-1 is at least 84 and sulphur content of the CUT-1 is below 50 ppmw. In one of the embodiment the CUT-1 corresponds to ultra-low sulfur products of high octane Gasoline and octane number of the CUT 1 is in the range of 84 to 90 units and sulphur content of the CUT 1 is in the range of 5 to 50 ppmw.

In yet another embodiment of the present invention, the CUT-2 corresponds to high aromatic Naphtha and octane number of the CUT-2 is at least 90 and sulphur content of the CUT-2 is below 50 ppmw. In one of the embodiment CUT-2 corresponds to high aromatic Naphtha and octane number of the CUT-2 is in the range of 90 to 105 units and sulphur content of the CUT-2 is in the range of 5 to 50 ppmw.

In yet another embodiment of the present invention, the feed is a high aromatic middle distillate.

In yet another embodiment of the present invention, the feed is diesel range hydrocarbon feedstock selected from (a) mineral petroleum oil; (b) Light Cycle Oil stream of FCC unit; (c) gas oil stream of delayed coker unit; (d) pyrolysis oil; (e) thermally cracked bio-sources or mixtures thereof.

In yet another embodiment of the present invention, the hydrotreating step is carried out at a pressure of about 25 to 75 barg and temperature of about 280 to 450° C. and at a LHSV of 0.1 to 5.0 $h^{-1}$.

In yet another embodiment of the present invention, the hydrocracking step is carried out at a same pressure as that of hydrotreating step.

In yet another embodiment of the present invention, the hydrocracking step is carried out at a temperature of 300 to 450° C. and at a LHSV of 0.1 to 5.0 $h^{-1}$.

In yet another embodiment of the present invention, the hydrocracking step is carried out at a conversion level that gives combined yield of CUT 1 and CUT 2 of above of about at least 30 wt %.

In yet another embodiment of the present invention, the CUT-2 is having monoaromatics and alkylated monoaromatics concentration more than 30 wt %.

In yet another embodiment of the present invention, the CUT-3 before oxidation step is having cetane number not more than 40. In one of the embodiment the CUT-3 before oxidation step is having cetane number in the range of 30 to 37.

In yet another embodiment of the present invention, the CUT-3 before oxidizing step is rich in a benzocycloparaffins and at least in the range of 10 to 30 wt % and in no case less than 10 wt %. In one of the embodiment benzocycloparaffins in the CUT-3 is more than 20 wt %. In another embodiment CUT-3 also includes paraffins, naphthenes, benzodicyclyparaffins, alkylaromatics, aromatics, diaromatics, triaromatics, etc. In one of the preferred embodiment benzocycloparaffins is naphtho-benzenes.

In yet another embodiment of the present invention, the CUT-3 stream is oxidized with oxidizing agent at a temperature in the range of 35 to 250° C., pressure in the range of 1 to 50 barg and reaction time of oxidation in the range of 0.1 to 36 hrs.

In yet another embodiment of the present invention, the oxidizing agent is selected from organic, inorganic, molecular oxygen or oxygen containing gases, ozone or ozone containing gas and mixtures thereof.

In yet another embodiment of the present invention, the oxidation product of the CUT-3 is partially recycled to selective oxidation step during oxidation step to increase the yield & selectivity of oxidized compounds in product and ratio of recycle feed to feed is between 1 to 20 vol/vol.

In yet another embodiment of the present invention, the cetane improvement of the CUT-3 after selective oxidation is between 2 to 15 units more than that the CUT-3.

In yet another embodiment of the present invention, the selective oxidation step is carried out over a catalyst selected from mixture of metal oxide and salts of organometallic oxide.

In yet another embodiment of the present invention, the catalyst for selective oxidation step comprises:
  a. a metal oxide, the metal of which selected from Fe, Cr, Cu and Co or their mixture impregnated on inert support;
  b. organometallic catalyst comprises salts of metal phthalocyanines impregnated on inert support material and the metal of organometallic complex is selected from Co, Fe and Cr.

In yet another embodiment of the present invention, the salts of metal phthalocyanines are selected from nitride, nitrate, chloride, sulfide, sulfate, sulfonate, amide or mixtures thereof.

In yet another embodiment of the present invention, the support material of catalyst for selective oxidation step is selected from activated charcoal, silica, silica/alumina, alumina or a mixture thereof.

DETAILED DESCRIPTION OF THE INVENTION

While the invention is susceptible to various modifications and alternative forms, specific embodiment thereof will be described in detail below. It should be understood, however that it is not intended to limit the invention to the particular forms disclosed, but on the contrary, the invention is to cover all modifications, equivalents, and alternative falling within the scope of the invention as defined by the appended claims.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

The terms "comprises", "comprising", or any other variations thereof, are intended to cover a non-exclusive inclusion, such that one or more processes or composition/s or systems or methods proceeded by "comprises . . . a" does not, without more constraints, preclude the existence of other processes, sub-processes, composition, sub-compositions, minor or major compositions or other elements or other structures or additional processes or compositions or additional elements or additional features or additional characteristics or additional attributes.

The present invention describes an integrated process comprising of hydrotreating, mild hydrocracking and selective oxidation reaction for producing high value products comprising of Low sulphur high octane light naphtha for gasoline pool, Heavy naphtha with high aromatic content particularly alkylbenzenes for petrochemical purpose and high Cetane ULSD for Euro-IV/V diesel pool from highly aromatic middle distillate range stream of cracker units like LCO from FCC units.

In one of the embodiment the present invention relates to an integrated process for upgradation of low value high aromatic feed stocks to high value products of High Octane Gasoline in the range of 84 to 90 unit, High Aromatic Naphtha in the range of 90 to 105 unit and High Cetane Diesel having cetane number of at least 42. More particularly the cetane number is enhanced by another 2 to 15 units.

An integrated process is disclosed for the production of ultra low sulfur products of high octane gasoline, high aromatic naphtha and high Cetane Diesel from high aromatic middle distillate range streams from any cracker units such as Light Cycle Oil (LCO) stream of Fluid catalytic cracking (FCC) units and comprising of subjecting the feed boiling between 200 to 400° C. and having at least 30 wt % multi-ring aromatics content subjected to hydrotreating for removal of heteroatoms like sulfur and nitrogen and at a pressure sufficient only for saturation of one ring of multi-ring aromatics. The effluent from hydrotreating is subjected to hydrocracking at same pressure of hydrotreating step above for selective opening of saturated ring of multi-ring aromatics. The effluent from hydrocracking is separated in CUT-1 boiling in the range 35 to 70° C., CUT-2 boiling in the range 70 to 200° C. and CUT-3 boiling in the above 200° C. The CUT-1 is recovered and sent to gasoline pool owing to its high content of iso-paraffins and hence high octane number. The CUT-2 is recovered as petrochemical feed stock owing to its high content of benzene & alkylbenzenes.

The CUT-3, which is having increased paraffins and naphthenes and also has naphtho-benzenes in sufficient quantities, is selectively oxidized in selective oxidation step in presence of catalyst, an oxidizing agent and operating conditions such that it results in diesel product with more enhanced Cetane.

Without being bound by theory, it is believed that in hydrocracking step some part of the feed is hydrocracked to smaller compounds having boiling point below 200° C., therefore feed need to boiling higher than 200° C. The diesel range feed stock is generally limited to higher boiling range of 400° C., therefore, the boiling range of feed specified is in the range of 200 to 400° C.

Without being bound by theory, it is believed that the present invention is not suitable for feed having lower than 30 wt % multi-ring aromatics. The higher multi-ring aromatics level is better for the present invention. Generally, the multi-ring aromatics are between 30 to 90 wt % in LCO.

It is also disclosed, alternatively that the effluent from hydrotreating step is mixed with the effluent from the hydrocracking step and the combined stream is fractionated in the CUT-1 boiling between 35 to 70° C., CUT-2 boiling between 70 to 200° C. in which the monoaromatics and alkylated monoaromatics are concentrated and CUT-3 boiling above 200° C. in which concentration of saturates i.e. paraffins and naphthenes significantly increased and also have benzocycloparaffins/naphtho-benzenes in sufficient quantities. Some part of this CUT-3 is sent to hydrocracking step being carried out at same pressure as that of hydrotreating. Remaining part of CUT-3 is recovered as the diesel and sent to selective oxidation step for further cetane enhancement.

In yet another disclosure, another alternative step is added to both of the above process configurations, in which, the part of the CUT-3 is recovered as diesel and subjected to hydrotreating before it is subjected to selective oxidation step for further cetane enhancement.

The present invention discloses a process for the production of high value streams like High octane motor gasoline, Petrochemical Feed Stocks and high Cetane ULSD from low value highly aromatic middle distillate range streams or any streams with boiling range preferably between 100 to 400° C., more preferably 140 to 400° C. and most preferably 200-400° C. containing high concentration of multi-ring aromatics preferably not more than 3 rings.

Figure 1:
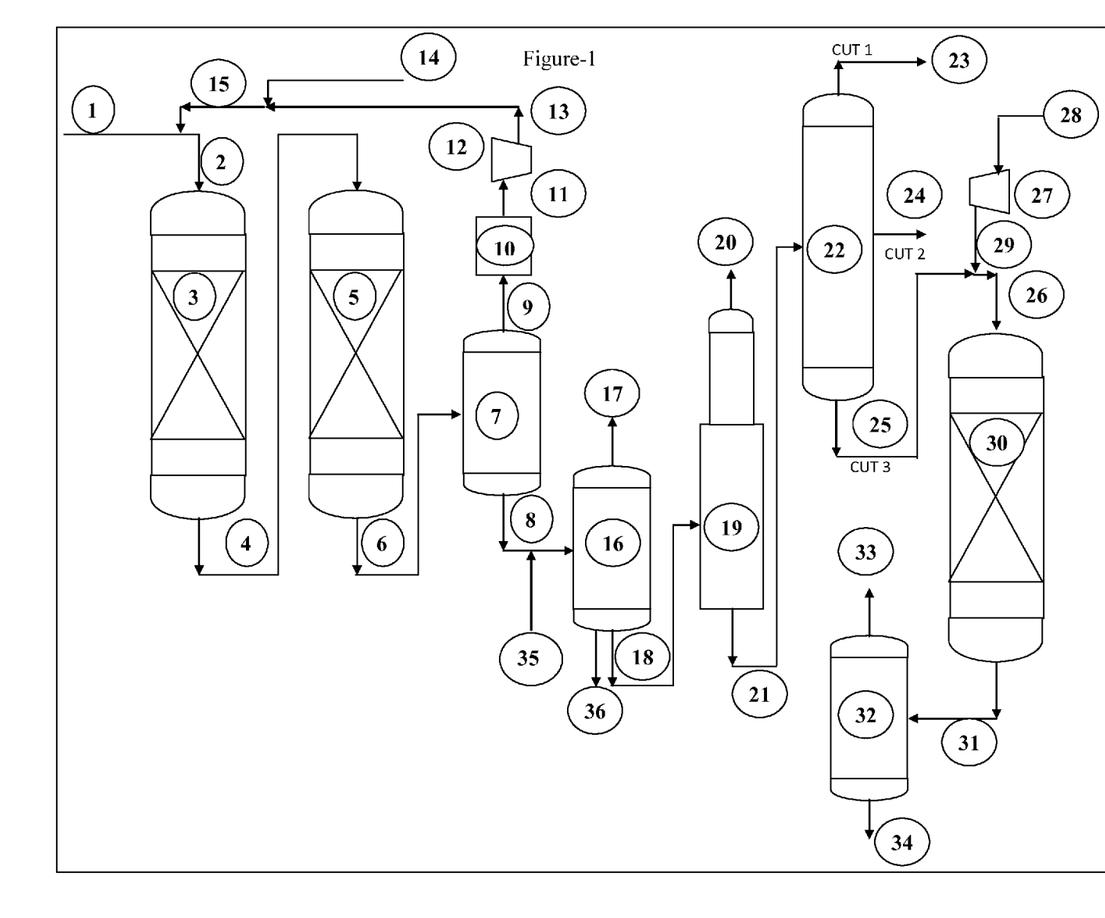
FIG. 1: Process Diagram for the production of high octane gasoline, high aromatic naphtha and high cetane diesel from high aromatic middle distillate range streams.

The process for the present invention is schematically described in the FIG. 1. The hydro carbonaceous feed containing high aromatic compounds, particularly di- and tri-ring aromatic is introduced into the process via line 1. The feed then mixed with hydrogen (line 15) is fed to the reactor 3 containing hydro treating catalyst via line 2. The hydro treated effluent from of reactor 3 is then introduced into the reactor 5 containing hydrocracking catalyst via line 4. The effluent of the hydrocracker reactor 5 via line 6 is flashed in a high pressure separator (HPS) 7. The gas stream rich in hydrogen is withdrawn from the HPS via line 9 and then amine washed 10 and send to recycle gas compressor 12 via line 11. The compressed gas is taken out from the compressor 12 via line 13. Before going to the reactor the fresh make hydrogen gas is introduced via line 14. The liquid from the HPS 7 is taken out via line 8 and further flashed at low pressure in a low pressure separator (LPS) 16. The gas mainly containing C1 and C2 is taken out from LPS 16 via line 17. The wash water is introduced in line 8 via line 35 and sour water is takeout from LPS via line 36. The hydrocarbon liquid from LPS 16 is withdrawn via line 18 and introduced in the stabilizer column 19. The dissolved gases comprising mainly of C3 and C4 components are withdrawn from the top of the stabilizer via line 20. The stable liquid is further routed to distillation column 22 via line 21. In the distillation column the entire liquid is fractionated into 3 cuts, (i) Light naphtha (35-70° C.) (CUT-1), (ii) Heavy Naphtha/Petrochemical heart Cut (70-200° C.) (CUT-2) and (iii) ULSD (200° C.+) (CUT-3). The CUT-1 is withdrawn from the distillation column via line 23. The petroleum heart cut i.e. CUT-2, which contains sufficient quantity of alkyl benzene is withdrawn via line 24 can be sent to the Petrochemical complex for aromatic extraction or can be used as gasoline pool blend since its RON is at least 90. The third cut i.e. CUT-3 is diesel range cut and is withdrawn from the column via line 25. The CUT-3 is then routed to oxidation reactor 30. The oxidation agent i.e. air is introduced into the system via line 28. The air is compressed in compressor 27 and mixed with CUT-3 via line 29. The compressed air and CUT-3 is then introduced into the reactor via line 26. The effluent of reactor 30 via line 31 goes to the de-gasifier 32, where dissolved and un-reacted oxygen is separated from the oxidized diesel. The oxygen is taken out from the degasifier via line 33 and the oxidized diesel is sent to tank yard via line 34. The oxidized diesel is high in Cetane number.

In the present invention, the hydrocarbonaceous feed stock boiling in the range of 100 to 400° C., more preferably 140 to 400° C. and most preferably 200-400° C. containing high concentration of multi-ring aromatic compounds preferably di- and tri-ring compounds is selected and hydrotreated for removing hetero atom impurities and more particularly the nitrogen containing compounds in the first step of this multistep process.

The operating conditions in hydrotreater are selected such that one aromatic ring in two ring aromatics and two rings in three ring aromatics are saturated. For this reason the pressure has to be lower side than those followed in conventional high pressure which are employed to saturate as much of the aromatics as possible. At the same time the hydrogenation function of the catalyst should be carefully tuned for the ring saturation at such low or medium pressures. The present invention, however, is not limited by the type of catalyst or selection of catalyst that is to be used in the hydrotreating step. Any suitable conventional hydrotreating catalyst which is able to perform the function of one aromatics ring saturation will suffice to use. The preferred pressure ranges are 20 to 100 barg, more preferably 25 to 75 barg. The other conditions of temperature, LHSV, can be selected from the wide range depending on the feed stock type and catalyst that is being employed. The temperature range that is preferred is 280 to 450° C. and more preferably 300 to 400° C. The preferred LHSV is 0.1 to 5 $h^{-1}$ and more preferable range is 0.2 to 2.5 $h^{-1}$. Similarly the preferred $H_2$ to hydrocarbon oil ratio is 100 to 600 $Nm^3/m^3$ and more preferred is 300 to 500 $Nm^3/m^3$.

Apart from saturation of one aromatic ring, the hydrotreating step is carried out to reduce the nitrogen levels in the feed stocks. The nitrogen compounds being the inhibitory to the acidic function of the hydrocracking catalyst of the hydrocracking step. The total nitrogen at hydrotreater effluent preferred is <50 ppmw and more preferably <20 ppmw. The low nitrogen level at hydrotreater outlet is desirable for maintaining high activity of the hydrocracker catalyst, since the nitrogen containing compounds have tendency to get adsorbed at the Acid sites of hydrocracker catalyst and thus reducing the activity of hydrocracking catalyst.

In one of the embodiments of the present invention, the effluent from hydrotreating is subjected to hydrocracking at same pressure of hydrotreating step above for selective opening of saturated ring of multi-ring aromatics. The advantage of using Hydrotreating step and Hydrocracking step at same pressure in present invention is that they are operated in series and therefore cost effective. Whereas, for different pressures the cost will be higher and processing scheme will be different. The effluent from hydrocracking is separated in CUT-1 boiling in the range 35 to 70° C., CUT-2 boiling in the range 70 to 200° C. and CUT-3 boiling in the above 200° C. The CUT-1 is recovered and sent to gasoline pool owing to its high content of iso-paraffins and hence high octane number. The CUT-2 is recovered as petrochemical feed stock owing to its high content of benzene & alkylbenzenes. The CUT-3, which is having increased paraffins and naphthenes and also has benzocycloparaffins/naphtho-benzenes in sufficient quantities, is selectively oxidized in selective oxidation step, in presence of catalyst, an oxidizing agent and operating conditions such that it results in diesel product with more enhanced Cetane. It is major highlight of the present invention that it produces three high quality and ultra low sulfur products at minimum possible hydrogen consumption than conventional hydrotreating and hydrocracking. The major hydrogen consumption comes from aromatics saturation. In present invention, instead of saturating all the aromatics, only one ring of the multi-ring aromatics is saturated and the effluent from hydrotreating is subjected to hydrocracking step to hydrocrack only one ring which is saturated in hydrotreating step and make it suitable for high octane gasoline and high aromatics naphtha, and for remaining unconverted (un-hydrocracked) portion of feed selective oxidation step is used for further cetane enhancement. Thus, offering the best upgradation solution for the LCO and other cracked stocks having significant proportion of aromatics and heteroatoms like sulfur and nitrogen.

In the present invention, the effluent from hydrotreater is directly sent to hydrocracker. The hydrotreater effluent low in nitrogen, preferably <50 ppmw and more preferably <20 ppmw is hydrocracked selectively for cracking/opening the side rings of the multi-ring aromatics preferably not more than 3 ring. The hydrocracking step is proposed to be carried out at the same pressure as that of hydrotreating pressure (first step) under the provisions of the present invention. The pressure of hydrocracking is kept low because of the necessity of leaving sufficient benzocycloparaffins/naphtho-benzenes which are boiling above 200° C., intact even after hydrocracking. So that they can be subjected to selective oxidation for cetane improvement. In one of the embodiment of the present invention, the pressure of hydrocracking is kept low for leaving at least 5 wt % benzocycloparaffins/naphtho-benzenes, more preferably at least 10 wt % benzocycloparaffins/naphtho-benzenes in hydrocracking effluent. In yet another embodiment of the present invention, higher the amount of benzocycloparaffins/naphtho-benzenes is better for selective oxidation and cetane enhancement. In one of the embodiment of the present invention, benzocycloparaffins/naphtho-benzenes is obtained in CUT-3 is more than 20 wt %. These hydrotreating pressures (preferably 30 to 100 barg, more preferably 25 to 75 barg) are very low when compared to conventional high pressure hydrocrackers having pressure range of 150 to 250 barg and still lower when compared to the conventional mild hydrocracking conditions which are being carried out at pressure range of 90 to 120 barg. The reason being such low pressures of 30 to 100 barg more preferably 25 to 75 barg is to prevent over saturation of aromatic rings and hydrocrack the saturated ring of two or more ring aromatics and stop secondary hydrocracking, if any.

The catalyst for this hydrocracking step can be selected from any conventional hydrocracking catalyst available in the field of art. The present invention is not limited by the selection of type of hydrocracking catalyst. Still, if one takes into account the feed stock characteristics and the pressure ranges that are involved, the mild hydrocracking catalysts are more preferable. It is still more preferable if the hydrogenation function of conventional mild hydrocracking is tuned for the improved hydrocracking performance.

The other conditions of temperature, LHSV, can be selected from the wide range depending on the feed stock type and catalyst that is being employed. The temperature range that is preferred is 250 to 420° C. and more preferably 300 to 400° C. The preferred LHSV is 0.1 to 5 h$^{-1}$ and more preferable range is 0.2 to 2.5 h$^{-1}$. Similarly the preferred H$_2$ to hydrocarbon oil ratio is 100 to 600 Nm$^3$/m$^3$ and more preferred is 300 to 500 Nm$^3$/m$^3$. The conversion for the hydrocracker reactor is defined as:

$$\text{Total Conversion(wt \%)} = \frac{(200° \text{ C.–in rector effluent}) - (200° \text{ C.–in hydrotreater inlet feed})}{(200° \text{ C.+in hydrotreater inlet feed})} \times 100$$

The Total Conversion level is maintained preferably between 25 to 40 wt % and more preferably between 40 to 50 wt % and most preferable between 50 to 60 wt %. The conversion affects yields of CUT-1 and CUT-2. The more the conversion, more is yields of CUT-1 and CUT-2. But rate of increase of yield of CUT-1 with increase in conversion level is more than the rate of increase of the yield of CUT-2. Further, this variation in yields of CUT-1 and CUT-2 may affect the concentrations of alkylbenzenes in CUT-2 and hence its aromatics and octane number.

In yet another embodiment of the present invention, the hydrotreater effluent is combined with the hydrocracker effluent and this combined effluent is sent to a fractionator. The feed to hydrocracker is the some part of the CUT-3 from the fractionator. This variation from the above embodiment further increases the amount of saturates and naphthenes in the CUT-3. This some part of the CUT-3 which is being sent to hydrocracker from fractionator can be whole CUT-3 or any fraction of CUT-3 depending on the severity of the processing required to maintain the quality of the CUT-3. The preferably 40 to 60 wt % of the CUT-3 is to be sent to hydrocracker.

Figure 2:
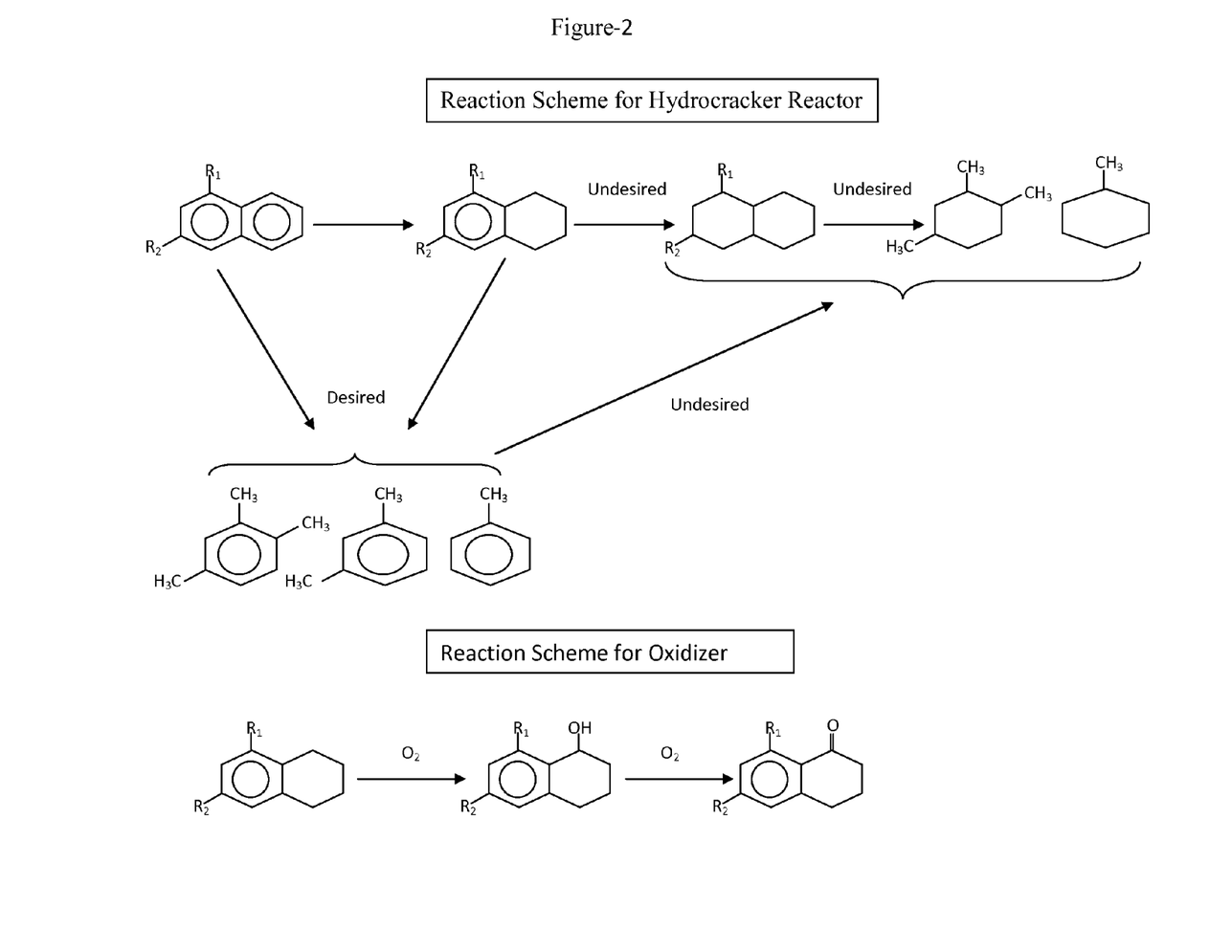
FIG. 2: Reaction Scheme for Hydrocracker reactor.

The reaction philosophy for the hydrocracker reaction mentioned in the embodiment is described in FIG. 2.

The hydrocracker reactor effluent separated into total gaseous fraction (Dry gas part and LPG) and total liquid part, the total liquid part is sent to a fractionator. In fractionator, the liquid fraction is further fractionated into three cuts Light Naphtha (CUT-1) (35 to 70° C.), Petrochemical Heart Cut (CUT-2) (70 to 200° C.) and ULSD (CUT-3) (200° C.+). If the hydrocracking step is operated at the preferred conversion levels of 50 to 60 wt % in the present invention, then the yield of total gas fraction obtained is below 5.0 wt %, more commonly below 2.0 wt % and most commonly below 1.0 wt %. The obtainable yield of CUT-1 (35 to 70° C.) is generally below 10 wt %, commonly below 7 wt % and most commonly below 5 wt %. The yield of CUT-2 (70 to 200° C.) should be generally be between 20 to 30 wt % more commonly between 30 to 40 wt % and mostly between 40 to 50 wt % are achievable under the provisions of present invention.

The levels of Total Conversion are flexible and are guided by the desired yield of particular product such as diesel (CUT-3) or lighters (CUT-2) as well as the concentration of alkylbenzenes in CUT-2. The Total conversion can be also guided by the demand and differential pricing of petrochemical products and diesel fuel.

The selectivity of the hydrocracker catalyst for the process mentioned in the embodiment is defined by the concentration of alkylbenzenes in CUT-2. Greater the concentration of alkylbenzenes in the Heart cut (CUT-2), better is the catalyst for the present performance duty. The commonly achievable concentration of alkylbenzenes is more than 40 wt % and most desired concentration is greater than 50 wt % under the provisions of present invention. The ratio of concentration of the naphthenic types of compounds to paraffinic compound is greater than 1 wt %, more commonly it is greater than 2 wt % and mostly greater 2.5 wt % are achievable and similarly the ratio of concentration of the iso-paraffin to n-paraffin is greater than 1.0, more commonly greater than 2.0 and mostly they are greater than 3 wt % in the heart cut under the process configuration of present invention. The achievable Octane number of CUT-2 is at least 90 units and more preferably greater than 95 units. The total sulphur in the CUT-2 obtainable is less than 10 ppmw.

In another embodiment of the invention, the octane number of the CUT-1, distillation range 35 to 70° C. is at least 85 units. The ratio of iso to normal paraffin in the CUT-1 commonly obtained is greater than 1 and more commonly greater than 2. The sulphur in the CUT-1 is less than 10 ppmw is obtained.

In yet another embodiment of the invention, the ULSD (CUT-3), distillation ranges 200° C.+ is enriched in benzocycloparaffins/Naphtho-benzene type of compounds. The Cetane number of the cut is in the range of 30 to 37 units and cannot be more than 40. The 95 vol % recovery for the cut is in the range of 340 to 360° C. and in no case it is greater than 360° C. The sulphur in the CUT-3 is generally obtained less than 50 ppmw, more commonly less than 25 ppmw and mostly less than 10 ppmw.

The CUT-3 rich in benzocycloparaffins/Naphtho-benzenes types of compounds at least in the range of 10 to 30 wt % and in no case less than 10 wt % is selectively oxidized in the oxidation reactor containing oxidation catalyst in presence of oxidizing agent/agents comprising of any type, organic, inorganic, molecular oxygen or ozone or combinations thereof, which supplies oxygen at the reaction conditions. The Cetane number of the oxidized product is improved at least by 2 to 15 units than the feed i.e. CUT-3.

In yet another embodiment of the present invention, the CUT-3 from the fractionator is hydrotreated again under similar operating conditions as in the first hydrotreating step before sending it to the selective oxidation step. This hydrotreating step may be required due to number of obvious reasons such as very high level of sulfur being observed so that the product is not meeting the diesel product specifications or the level of nitrogen is very high so that the product color is very dark. This is due the fact that the sulfur and nitrogen compounds get concentrated in the heavier portion of the fraction. The additional hydrotreating step can further boost the cetane number, which will be getting further improved in the downstream selective oxidation step. It is may be observed that the reasons for this obvious variation of the above configuration are no way going affect the downstream selective oxidation step.

The oxidizing agent for the selective oxidation reaction of CUT-3 can be of any type, viz. organic, inorganic, molecular oxygen or ozone that can supply oxygen at the reaction conditions. The most preferred oxidizing agent is compressed air because of low cost and abundance.

The selective oxidation can be carried out in any type of reactor, such as, but not limited to, plug flow (PFR) or continuous stirred tank reactor (CSTR). The most preferred reactor system is PFR with fixed bed catalyst system. The feed is brought in contact with oxidizing agent at a temperature between 35 to 250° C. in the presence or absence of a catalyst. The reaction time for selective oxidation is high, between of 0.1 to 36 hours in absence of catalyst and in presence of catalyst the reaction time is reduced and also selectivity is improved.

The selective oxidation of the CUT-3 is done to introduce oxygen in the form of —OH group or keto group (═O) at the benzylic position of the benzocycloparaffins/Naphtho-benzene types of compounds distributed over the entire distillation range of CUT-3. The introduction of oxygen molecule at benzylic position of the benzocycloparaffins/naphtho-benzenes improves the Cetane of the compounds at least in the range of 10-20 units depending on the type of group and the particular compound and in turn improves the overall Cetane of the CUT-3 by 2 to 15 units upon selective oxidation. The concentration of oxygen containing compound in the oxidized product is below 1 wt %. The concentration of oxygen containing compounds is always below 10 wt % in present invention. The density increase of the oxidized product is not more than 0.01 g/cc.

In present invention, the selective oxidation step is carried out in the presence of a catalyst such as derivative of organometallic complex of any transition metal and more preferably of Fe, Cr, Cu and Co or mixtures thereof. The derivatives of organometallic complexes can be selected from but not limited to nitride, nitrate, chloride, sulfide, sulfate, sulfonate, amides or mixtures thereof. The organometallic complex compounds is impregnated on inert supports of silica, silica/alumina, activated carbon or any other suitable support by the procedures known in the art in such a way that total compound constitutes 0.1 to 10 wt % of total catalyst. It has been found that organometalic catalysts have better selectivity for oxidizing the molecules which enhances cetane on oxidation even at lower concentrations.

In the invention, organometallic catalyst can be used in combination with an oxide based catalyst. The metal oxides are generally combinations of two or more oxides selected from Fe, Cr, Cu and Co. The total metal content of oxide catalyst is 1 to 30 wt %; the oxides of metals are of two or more different metals each constituting 1 to 25 wt % of total catalysts. The combination of organometallic catalyst and oxide based catalyst can be prepared in various combinations thereof. The organometallic complex catalysts and oxide catalysts when used in combination are in a specific ratio in the range of 0.5:1 to 1:1 w/w.

It may be noted here that before the selective oxidation step cetane number of CUT-3 that is the diesel product is always below 35 to 37 units but after selective oxidation step, the cetane number is improved by another 2 to 15 units. Therefore, it is pertinent to mention that the selective oxidation steps is the integral and necessary part of the present invention if the significant improvement in cetane number is desired for blending of the upgraded LCO and other cracked stocks with diesel pool in more cost effective way. The selective oxidation step on its part is improving the cetane number without affecting any other property of the CUT-3.

It is further advantage of the present invention that it yields three high quality and ultra low sulfur products at minimum hydrogen consumption possible, each having entirely different characteristics and uses. The CUT-1 is having large proportion of iso-paraffins and thus having moderate to high octane number and can be good blending stock for the gasoline pool. The CUT-2 is having very high concentrations of alkylbenzenes and hence can be a high value petrochemical feedstock, alternatively it can be a good blending stream for gasoline pool, since owing to its high alkylbenzene content it is having very high octane number. Third product, i.e., CUT-3 after selective oxidation is having highest achievable cetane number hence can be a good quality blending stock for diesel pool. It is also befitting to mention here that the processing scheme can be altered and varied as per the needs of the individual product demand and pricing prevailing. Since the final cetane improvement is achieved by means of selective oxidation and not by hydrotreating, the cost savings in terms of very high pressure hydrotreater and cost savings in terms of costly hydrogen make the process much more attractive economical option.

The following non-limiting examples illustrate in detail about the invention. However, they are, not intended to be limiting the scope of the present invention in any way.

Example-1

The aromatic rich carbonaceous stream of catalytic cracking unit (LCO) has been used as feed stock for hydrotreating. The Characterization of the feed is given in Table-1. The hydrotreating reaction has been carried out at 360° C. temperature, 50 barg $H_2$ partial pressure, 1 $h^{-1}$ LHSV and 400 $Nm^3/m^3$ hydrogen to oil ratio. The properties of the hydrotreated product is given in Table-2. The product obtained is having sulfur content of 53 ppm and cetane number of 30. The cetane number gain of about 5 units obtained in hydrotreating step.

TABLE 1

| Feed Properties (Example-1) | |
|---|---|
| Sulphur by XRF (D 2622), ppmw | 8100 |
| Nitrogen (D 4629), ppmw | 234 |
| Density (D 4053), g/cc | 0.8768 |
| SimTBP (D 2887), wt % | T (° C.) |
| 10 | 151 |
| 30 | 193 |
| 50 | 222 |
| 90 | 326 |
| 95 | 347 |
| Analysis Technique: Mass Spectrometry | Wt % |
| Saturates | 26.38 |
| Total Aromatics | 73.62 |
| Aromatics types, wt % | |
| Mono-Aromatics | 35.17 |
| Di-Aromatics | 36.31 |
| PAH | 2.14 |
| Cetane Number (D 613) | 25 |

TABLE 2

Hydrotreating Product Properties (Example-1)

| | |
|---|---|
| Sulphur (D 5453), ppmw | 53 |
| Nirtogen (D 4629), ppmw | 1 |
| Density (D 4053), g/cc | 0.8527 |

| Sim TBP (D2887), wt % | T (° C.) |
|---|---|
| 10 | 188 |
| 30 | 215 |
| 50 | 230 |
| 90 | 307 |
| 95 | 338 |

| Analysis Technique: Mass Spectrometry | wt % |
|---|---|
| Saturates | 36.23 |
| Total Aromatics | 63.77 |
| Aromatics types, wt % | |
| Mono- Aromatic | 48.74 |
| Di-Aromatics | 14.53 |
| Poly Aromatics | 0.50 |
| Cetane Number (D 613) | 30 |

Example-2

Similar to example-1 the aromatic rich stream of catalytic cracking unit (characterization given in Table-1) has been hydrotreated and then hydrocracked. The hydrotreating reaction has been carried out at 360° C. temperature, 50 barg $H_2$ partial pressure, 1 $h^{-1}$ LHSV and 400 $Nm^3/m^3$ hydrogen to oil ratio. The hydrotreater reactor effluent is routed to hydrocracker reactor. The hydrocracking reaction has been carried out at 370° C. temperature, 50 barg $H_2$ partial pressure, 0.67 $h^{-1}$ LHSV and 400 $Nm^3/m^3$ hydrogen to oil ratio. The yield pattern is given in Table-3. The properties of the hydrocracker products are given in Table-4 to 6. The hydrocracking product obtained is separated in three cuts by distillation. The yield of CUT-1 obtained is 3.99 wt % with sulfur content of less than 10 ppm and octane number of 86. The yield of CUT-2 obtained is 47.2 wt % with sulfur content of 22 ppm and octane number of 91. The aromatics of CUT-2 mainly constituted of 39 wt % monoaromatics (benzenes and alkyl benzenes) and 42.36 wt % naphthenes. Therefore, this cut is highly suitable feed stock for petrochemicals feed. Moreover, the iso-paraffins are about 14.18 wt % against the n-paraffins of 4.43 wt %, which along with high aromatics and naphthenes content make the CUT-2 equally suitable as a gasoline product. The yield of CUT-3, which is diesel range stream, is 49.02 wt % with sulfur content of 29 ppm and cetane number of 35. This means the cetane number gain of another 5 units when compared to hydrotreating product (Table-2, Example-1).

TABLE 3

Product Yields (Example-2)

| Streams | Yield, wt % |
|---|---|
| Off Gas | 0.26 |
| LPG | 0.69 |
| Light Naphtha (IBP-70° C.), CUT-1 | 3.99 |
| Petrochemical Heart Cut (70-200° C.), CUT-2 | 47.2 |
| Diesel (200° C.+), CUT-3 | 49.02 |
| Total | 101.6 |
| Chemical Hydrogen consumption | 1.6 |

TABLE 4

Product CUT-1 Properties of Example-2
(for yield of CUT-1 see Table-3)

| Properties | CUT-1 |
|---|---|
| Density (D 4053), g/cc | 0.7012 |
| Sulphur (D 5453), ppmw | <10 |
| Nitrogen (D 4629), ppmw | ND |
| Octane Number (D 2699) | 86 |

| SimTBP (D 2887) | ° C. |
|---|---|
| 10 | 35 |
| 30 | 57 |
| 50 | 74 |
| 90 | 122 |
| 95 | 124 |

TABLE 5

Product CUT-2 Properties of Example-2
(for yield of CUT-2 see Table-3)

| Properties | CUT-2 |
|---|---|
| Density (D 4053), g/cc | 0.7954 |
| Sulphur (D 5453), ppmw | 22 |
| Nirtogen (D 4629), ppmw | 1 |
| Octane Number (D 2699) | 91 |

| SimTBP (D 2887) | ° C. |
|---|---|
| 10 | 105 |
| 30 | 139 |
| 50 | 162 |
| 90 | 196 |
| 95 | 205 |

| Analysis technique: GC-MS | wt % |
|---|---|
| Alkylbenzenes (C0-C4 Alkyl chains) | 39.03 |
| N-Paraffins | 4.43 |
| Iso-Paraffins | 14.18 |
| C5 Naphthenes (C1-C3 alkyl chains) | 18.11 |
| C6 Naphthenes (C1-C3 alkyl chains) | 24.25 |

TABLE 6

Product CUT-3 Properties of Example-2
(for yield of CUT-3 see Table-3)

| Properties | CUT-3 |
|---|---|
| Density (D 4053), g/cc | 0.8703 |
| Sulphur (D 5453), ppmw | 29 |
| Nirtogen (D 4629), ppmw | 1 |
| Cetane Number (D 613) | 35 |

| SimTBP (D 2887) | ° C. |
|---|---|
| 10 | 206 |
| 30 | 227 |
| 50 | 250 |
| 90 | 361 |
| 95 | 383 |

Example-3

The CUT-3 of Example-2 is selectively oxidized in presence of oxidation catalyst (Cobalt based organometallic complex (1 wt %) impregnated on activated carbon) at temperature of 100° C., Air pressure 20 bar (g) and Air to Oil ratio of 200 $Nm^3/m^3$. The properties of the oxidized product are tabulated in Table-5. The product obtained is having all the properties essentially same as CUT-3 of Example-2, only cetane number has been increased due to selective oxidation from 35 to 42. This means cetane number gain of 7 units has been obtained.

TABLE 7

Product Properties (Example-3)

| Properties | CUT-3 after selective oxidation |
|---|---|
| Density, g/cc | 0.8741 |
| Sulphur (D 5453), ppmw | 29 |
| Nirtogen (D 4629), ppmw | 5 |
| Cetane Number (D 613) | 42 |
| SimTBP (D 2887) | ° C. |
| 10 | 205 |
| 30 | 230 |
| 50 | 250 |
| 90 | 355 |
| 95 | 380 |

We claim:

1. An integrated process for production of high octane gasoline (gasoline having octane number greater than 84), high aromatic naphtha (naphtha having octane number more than 90 and mono-aromatics and alkylated mono-aromatics concentration more than 30 wt %) and high cetane diesel (diesel having cetane number more than 42), the process comprising:
    a) subjecting a feed to a hydrotreating step at a predetermined pressure to obtain a first effluent having a reduced quantity of hetero-atoms compared to the feed, the feed comprising at least 30 wt % multi-ring aromatics and having a boiling point between 200 to 400° C., wherein the predetermined pressure is capable of saturating one or more rings of multi-ring aromatics while leaving unsaturated one or more rings of the multi-ring aromatics;
    b) subjecting the first effluent to a hydrocracking step at the predetermined pressure to obtain a second effluent, the hydrocracking step resulting in selective opening of at least one saturated ring of the multi-ring aromatics;
    c) separating the second effluent into a CUT-1, a CUT-2 and a CUT-3, with the CUT-1 having a boiling point between 35 to 70° C., the CUT-2 having a boiling point between 70 to 200° C. and comprising a concentration of mono aromatics and alkylated mono aromatics and the CUT-3 having a boiling point above 200° C. and comprising an enhanced concentration of saturates, wherein:
        the CUT-1 corresponds to said high octane gasoline, the octane number of the CUT-1 is at least 84, and a sulphur content of the CUT-1 is below 50 ppmw; and
        the CUT-2 corresponds to said high aromatic naphtha, the octane number of the CUT-2 is at least 90, and a sulphur content of the CUT-2 is below 50 ppmw; and
    d) subjecting at least a part of the CUT-3 to a selective oxidation step to in the presence of a catalyst, and an oxidizing agent to obtain said high cetane diesel range product (hydrocarbon liquid having boiling range between 200–400° C.).

2. The process as claimed in claim 1, wherein the feed is a high aromatic middle distillate or a diesel range feedstock selected from (a) mineral petroleum oil; (b) Light Cycle Oil stream of FCC unit; (c) gas oil stream of delayed coker unit; (d) pyrolysis oil; (e) thermally cracked bio-sources or mixtures thereof.

3. The process as claimed in claim 1, wherein the hydrotreating step is carried out at a pressure of about 25 to 75 barg and temperature of about 280 to 450° C. and at a LHSV of 0.1 to 5.0 $h^{-1}$.

4. The process as claimed in claim 1, wherein the hydrocracking step is carried out at a same pressure as that of hydrotreating step at a temperature of 300 to 450° C. and at a LHSV of 0.1 to 5.0 $h^{-1}$.

5. The process as claimed in claim 1, wherein the hydrocracking step is carried out at a conversion level that gives combined yield of CUT 1 and CUT 2 of above of about at least 30 wt %.

6. The process as claimed in claim 1, wherein the CUT-2 is having monoaromatics and alkylated monoaromatics concentration more than 30 wt %.

7. The process as claimed in claim 1, wherein:
    the CUT-3 having cetane number not more than 40 before oxidation step; and
    the CUT-3 before oxidizing step is rich in a benzocycloparaffins and at least in the range of 10 to 30 wt %.

8. The process as claimed in claim 1, wherein the CUT-3 stream is oxidized with oxidizing agent at a temperature in the range of 35 to 250° C., pressure in the range of 1 to 50 barg and reaction time of oxidation in the range of 0.1 to 36 hrs.

9. The process as claimed in claim 1, wherein the oxidizing agent is selected from organic, inorganic, molecular oxygen or oxygen containing gases, ozone or ozone containing gas and mixtures thereof.

10. The process as claimed in claim 1, wherein the oxidation product of the CUT-3 is partially recycled to the selective oxidation step during the oxidation step to increase the yield and selectivity of oxidized compounds in the product wherein the recycle ratio of oxidized product to feed (CUT-3) may vary from 1 to 20 vol %.

11. The process as claimed in claim 1, wherein the cetane improvement of the CUT-3 after selective oxidation is between 2 to 15 units more than that the CUT-3.

12. The process as claimed in claim 1, wherein the selective oxidation step is carried out over a catalyst selected from mixture of metal oxide and salts of organometallic oxide.

* * * * *